United States Patent [19]

Ray

[11] Patent Number: 5,410,409
[45] Date of Patent: Apr. 25, 1995

[54] SEARCH ROUTINE FOR ELLIPSOMETERS

[75] Inventor: Michael Ray, Winooski, Vt.

[73] Assignee: International Business Machines Corporation, Armonk, N.Y.

[21] Appl. No.: 752,818

[22] Filed: Aug. 30, 1991

[51] Int. Cl.$^6$ .............................................. G01J 4/00
[52] U.S. Cl. ..................... 356/369; 356/376; 356/382
[58] Field of Search ............... 356/369, 381, 382, 378, 356/376

[56] References Cited

U.S. PATENT DOCUMENTS 4,627,734 12/1986 Rioux ................................. 356/376
4,695,162 9/1987 Itonaga et al. ...................... 356/369

OTHER PUBLICATIONS

Niven, Ivan. *Calculus, An Introductory Approach*, D. Van Nostrand Company, Inc. Princeton, N.J. copyright 1961, pp. 1–3, 90–96.

Primary Examiner—Richard A. Rosenberger
Attorney, Agent, or Firm—Francis J. Thornton

[57] ABSTRACT

A method of locating a predetermined variation in the surface of a film such as selected depression or elevation on a film deposited on a surface and for measuring the depth of the depression or height of the elevation comprising the steps of establishing a datum plane based on the average level of the surface of the film, scanning the surface of the film with a laser beam until a predetermined variation from said datum plane is located, on the surface of the film, incrementally stepping the laser beam around and across the located variation, measuring the beam reflected at various points along the variation to determine the contour of the variation by establishing the slope of the variation between various measurements, establishing the apex of an elevation or bottom of a depression by determining when the measured slope goes to zero, and measuring the height of the established apex or depth of the established bottom of the depression with respect to the established datum plane of the film.

4 Claims, 6 Drawing Sheets

SEARCH ROUTINE FOR ELLIPSOMETERS

DESCRIPTION

This invention pertains to a method of locating changes in altitude of a transparent film on the surface of an opaque device. More specifically, the invention pertains to a method for locating and measuring the size of variations on the surface of a film with respect to an established base line. The variations may be in the form of a depression or an elevation on the film. The invention is particularly useful with semiconductor integrated circuit devices which have convoluted topographies.

DESCRIPTION OF THE PRIOR ART

A variety of known techniques have been created for measuring the thicknesses of films deposited on a body. Many of these use radiant energy beams and in particular use laser beams.

A current method employs the use of ellipsometers which are equipped with polarizing prisms and retardation plates and are used primarily in the analysis of elliptically polarized light reflected from the surfaces of thin evaporated films. In such ellipsometers, a beam of columnated laser light is directed first through a polarizer and then through a quarter wave retardation plate to the film under test from which it is reflected. The reflected beam is then directed through a second polarizer or analyzer and two of the three optical elements are interactively rotated so as to produce extinction of the beam exiting the polarizer or analyzer. The angular positions of the elements are accurately measured and used to determine the thin film thicknesses.

The incident light striking the surface of the sample being measured at a given angle is reflected at different amplitudes depending upon the angle of polarization. The relative amplitude and relative phase between the orthogonal pair of waves describes a polarization state. Thus, knowing the incident angle, the index of refraction of the material and the polarization state of the incident beam, provides information for establishing the thickness of the film.

A different method of measuring film thicknesses involves the impinging of a single wavelength to the surface of a sample and measuring both the intensity of the incident beam and that of the reflected beam. Again, utilizing the known angle of incidence, the index of refraction of the material, and the wavelength of the beam, the polarization state of the reflecting beam to that of the incident beam gives the change of polarization and through mathematical calculation the thickness of the film can be determined.

In these prior art systems, although a gross thickness of the films can be determined, the depth of selected depressions or the height of selected elevation varying from this gross thickness measurement cannot be readily and accurately determined.

Accordingly, the present invention is directed toward a method of readily determining and accurately measuring the depths of selected depressions in the surface of the film or the heights of selected elevations above the surface of the film which is under investigation.

More specifically, it is an object of the present invention to provide a method for locating a selected depression in or elevation on a film, deposited on a surface of a semiconductor device, and for measuring the depth of the located depression or the height of the located elevation with respect to the surface of the film.

SUMMARY OF THE INVENTION

The above and other objects of the invention are met by providing a method of locating a predetermined variation in the surface of a film such as selected depression or elevation on a film deposited on a surface and for measuring the depth of the depression or height of the elevation comprising the steps of establishing a datum plane on the surface of the film, scanning the surface of the film with a laser beam until a predetermined variation from the datum plane measurement is located, on the surface of the film, incrementally stepping the laser beam around and across the located variation, measuring the beam reflected at various points along the variation to determine the contour of the variation by establishing the slope of the variation between various measurements, establishing the apex of an elevation or bottom of a depression by determining when the measured slope goes to zero, and measuring the height of the established apex or depth of the established bottom of the depression with respect to the established base line on the scanned surface of the film.

The invention can also be utilized to further locate a particular variation on a surface by comparing the measured value of the established apex of the elevation or the bottom of the depression with a preselected value. Further, the position of any located variations can be recorded to provide a map of the topology of the film under study.

The invention will be better understood from the following description taken in conjunction with the drawings.

DESCRIPTION OF THE PREFERRED EMBODIMENT

Figure 1:
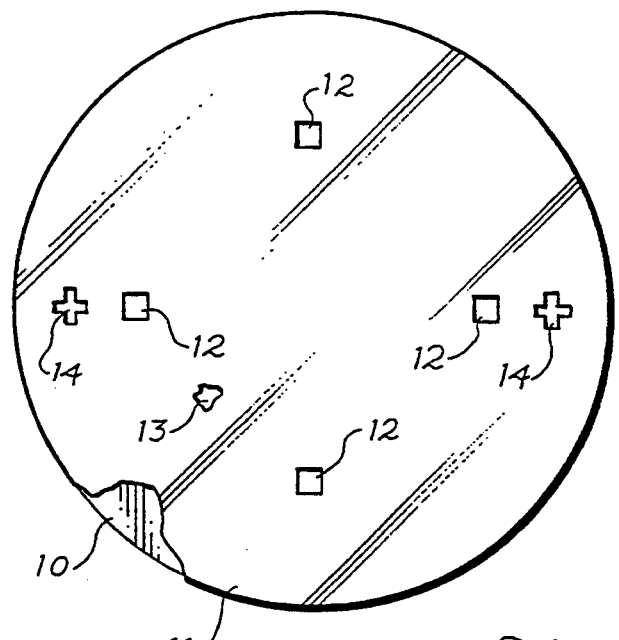
FIG. 1 is a top view of a large semiconductor wafer which has an oxide film deposited on its surface in which a series of depressions and protrusions have been created.

FIG. 1 shows a sectional view of a large scale integrated circuit configuration formed of a semiconductor substrate 10, such as silicon, having a film 11 on a major surface thereof. This film 11 may be, for example, any transparent or semi-transparent film such as an oxide. Also, the film 11 can have a plurality of variations on the surface thereof. In one instance these variations in the surface can be depressions or holes 12 and 13 formed therein. These depressions 12 and 13 can either be deliberately created therein such as formed openings 12 or inadvertently created as shown by the irregular defect 13. In either event the present invention is especially directed towards locating the position and measuring the extent of such variations. In the case of the deliberately formed openings 12 it is especially desirable to assure that they are at the desired locations and are of the proper depth. In the case of defect depression 13 it is desirable to determine its location and depth to determine its possible impact on or yield.

Figure 2:
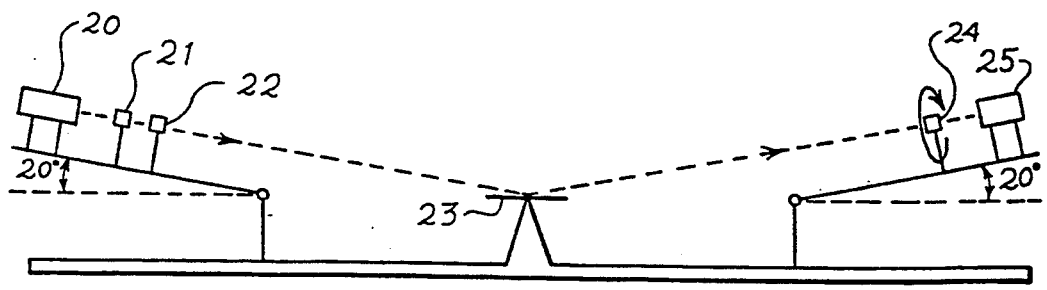
FIG. 2 is a schematic of a rotating analyzer ellipsometer as may be used to practice the present invention.

In any case the present invention uses a rotating analyzer ellipsometer as shown in FIG. 2, to scan the film, and thus to detect the location and depth of such depressions.

The present invention can also be employed to detect the absence of planned or desired openings which should have been provided in the surface and its effect on the yield can also be determined.

The invention can also be used to identify the location of a protrusion 14 such as might be formed by a deposit on or beneath the film 11.

The rotating analyzer ellipsometer (FIG. 2) used in the present invention is one that uses light from laser 20 which is polarized by polarizer 21, passed through a quarter wave plate 22, directed against the sample 23 and reflected therefrom through a synchronously rotating analyzer 24 to detect with detector 25 the state of polarization of light after its reflection from a surface under measurement. A basic ellipsometer can be readily modified to function as a rotating analyzer ellipsometer by the addition of a new assembly for the analyzer so that it can be rotated around the beam axis by a synchronous motor together with an electronic detection system capable of deriving the parameters that describe the reflected polarization ellipse from the periodic variations of the light flux transmitted by the rotating analyzer. Such automatic systems that employ both analog and digital signal detection are well known and have been described in the literature.

FIG. 2 is a schematic of the mechanical and optical layout of one such ellipsometer. The instrument is constructed to operate at a fixed angle of incidence of 20° and also in the direct path configuration. Three settings of 0° (for initial alignment), 12° (for increased sensitivity for the detection of films less than 300 angstroms in thickness) and 45° ($SiO_2$ films 300–1300 angstroms) are used for the polarizer. The analyzer is driven by a synchronous motor (not shown) at a 50 rps constant speed. The light beam leaving the rotating analyzer passes through a diffuser (not shown) and fiber-optic bundle (not shown) to depolarize the light incident on the cathode of the photo-multiplier detector 25, thereby avoiding a polarization-dependent photoelectric effect.

One scheme for data acquisition uses a dual output optical angular encoder mounted on the same shaft with the rotating analyzer sensing the instantaneous azimuth of the analyzer. One output of the encoder provides a synchronizing pulse each complete rotation, and the other output gives 256 equally spaced pulses per revolution. These pulses trigger an analog-to-digital (A/D) converter to sample the analog signal from the photomultiplier detector (25), converting it to digital form, to be read by an on-line computer. The digital intensity data at 256 equally spaced angular positions of the rotating analyzer is subsequently Fourier analyzed to determine the reflected polarization by a least-square fit of a sine-wave.

Figure 3:
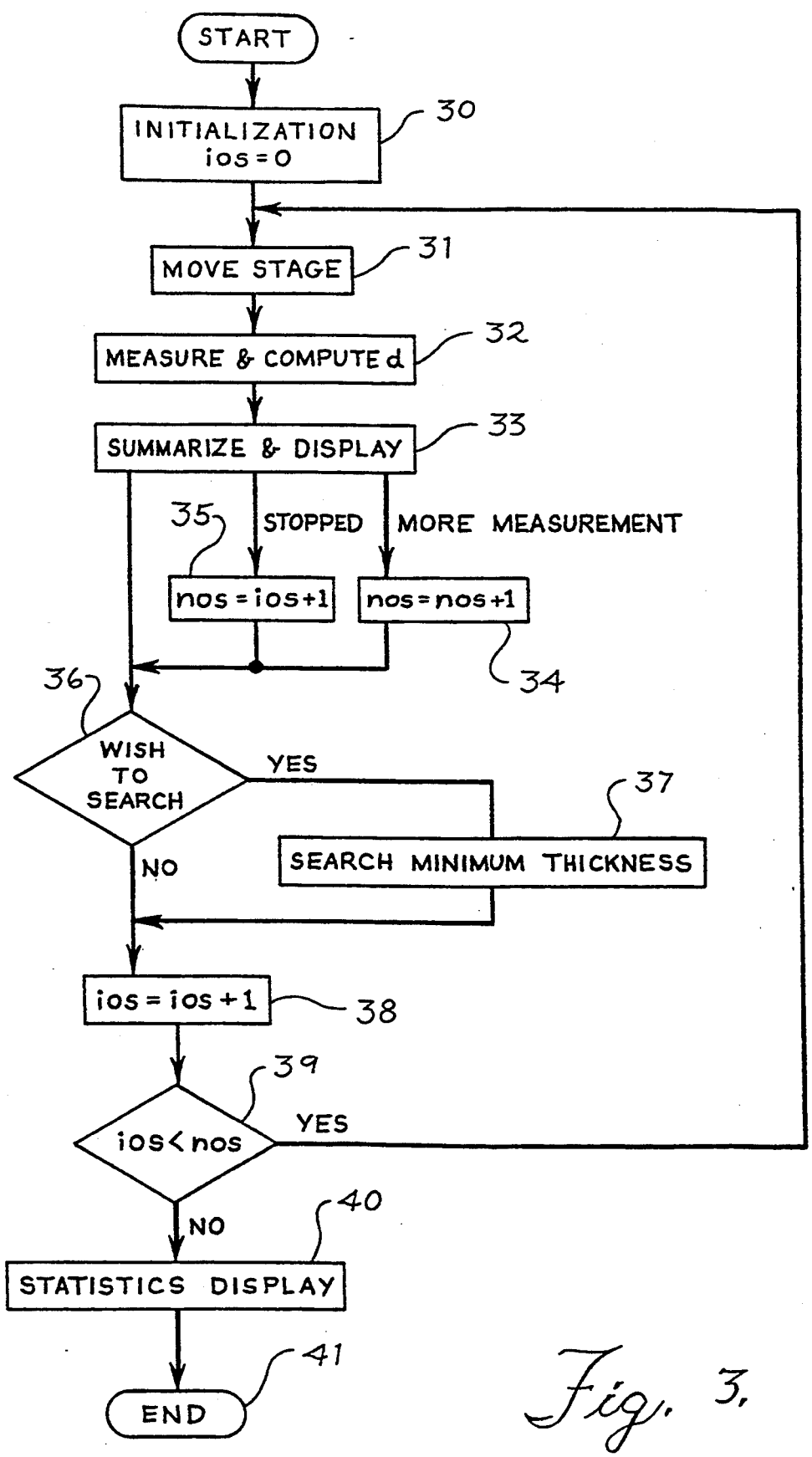
FIG. 3 is a flow chart used to describe a preferred embodiment of the invention by which the depression illustrated in FIG. 5 was measured.
Figure 4:
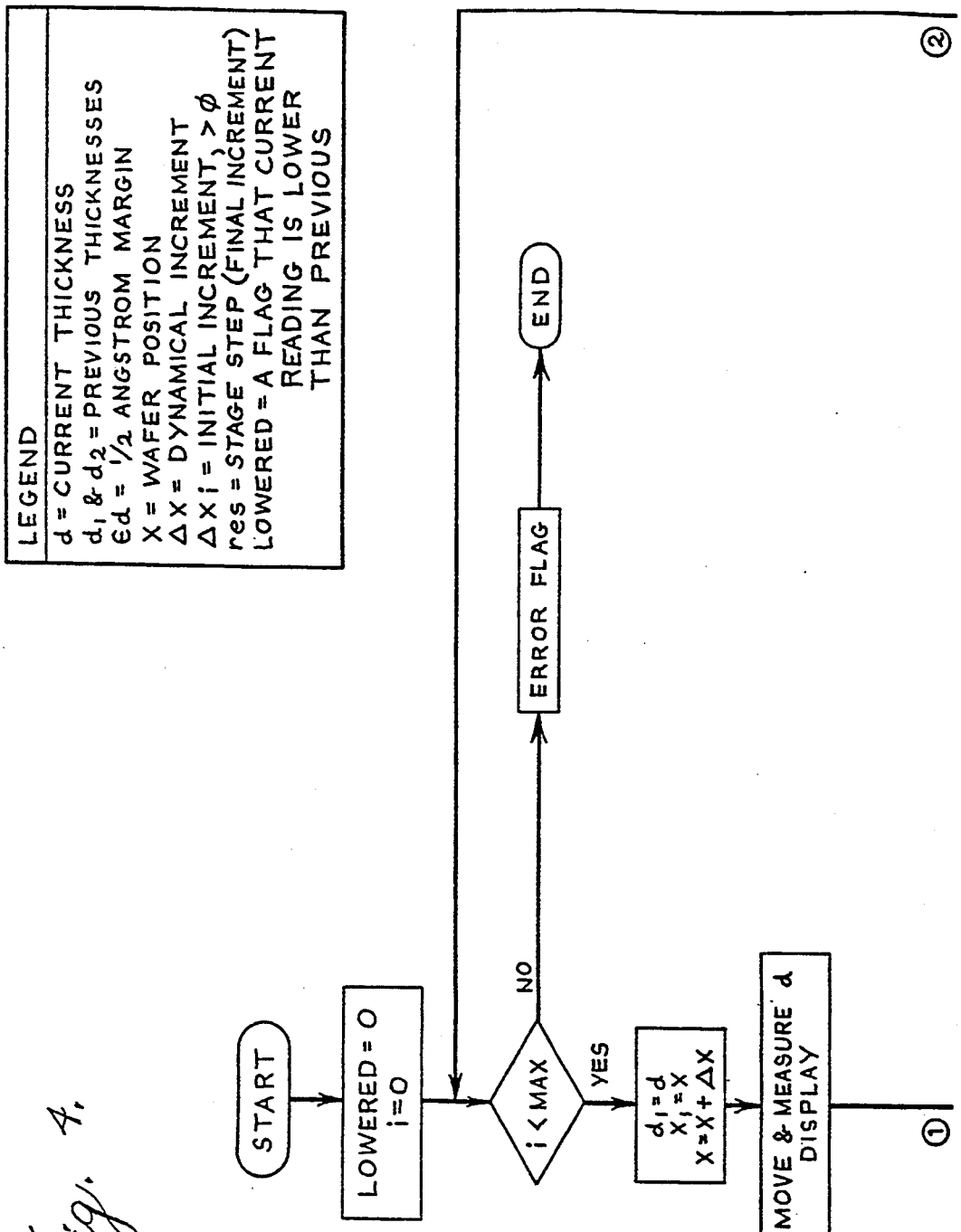
FIG. 4 is a detailed flow chart of that portion of the flow chart of FIG. 3 where the repetitive search step is set forth in significant detail.
Figure 4:
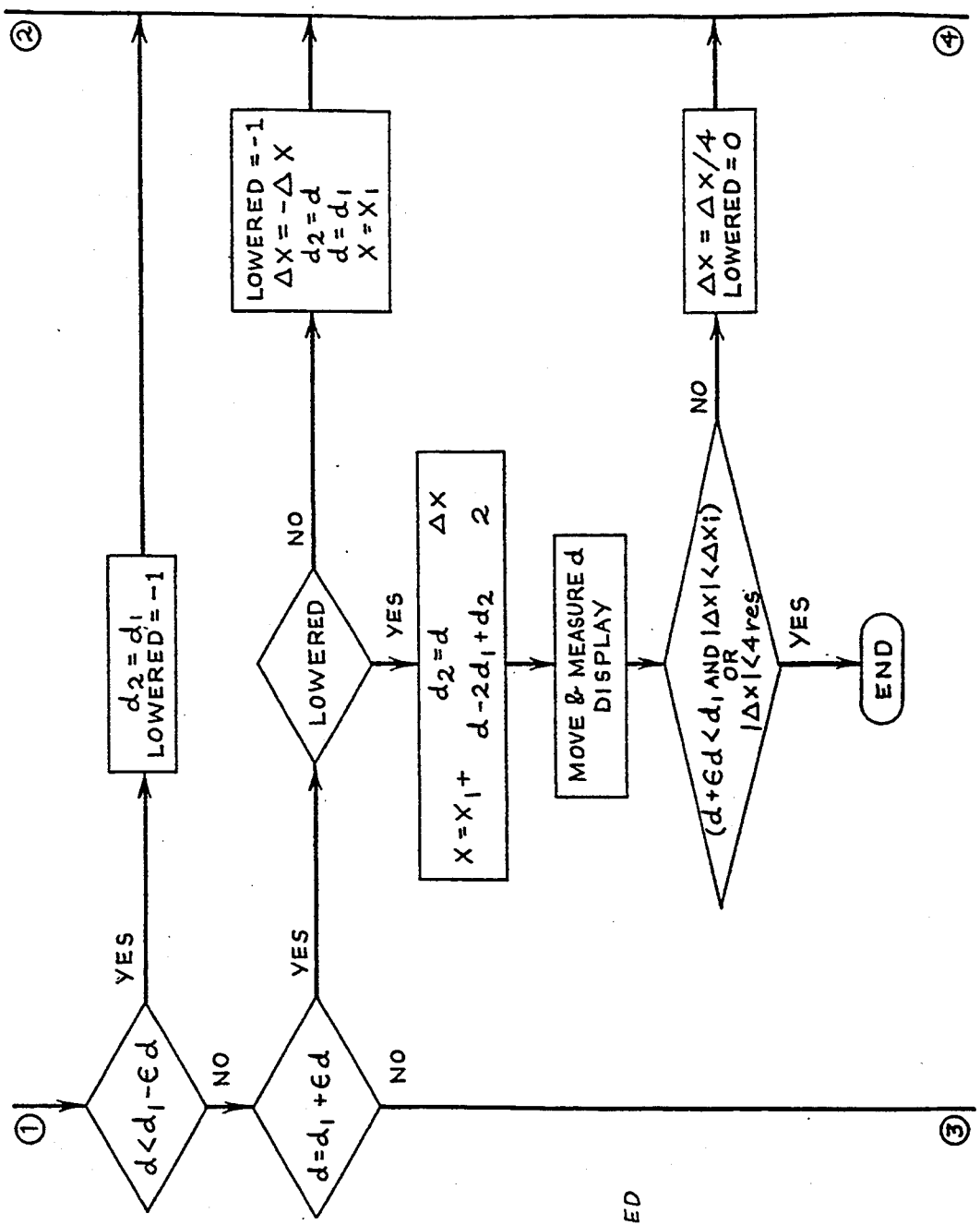
Figure 4:
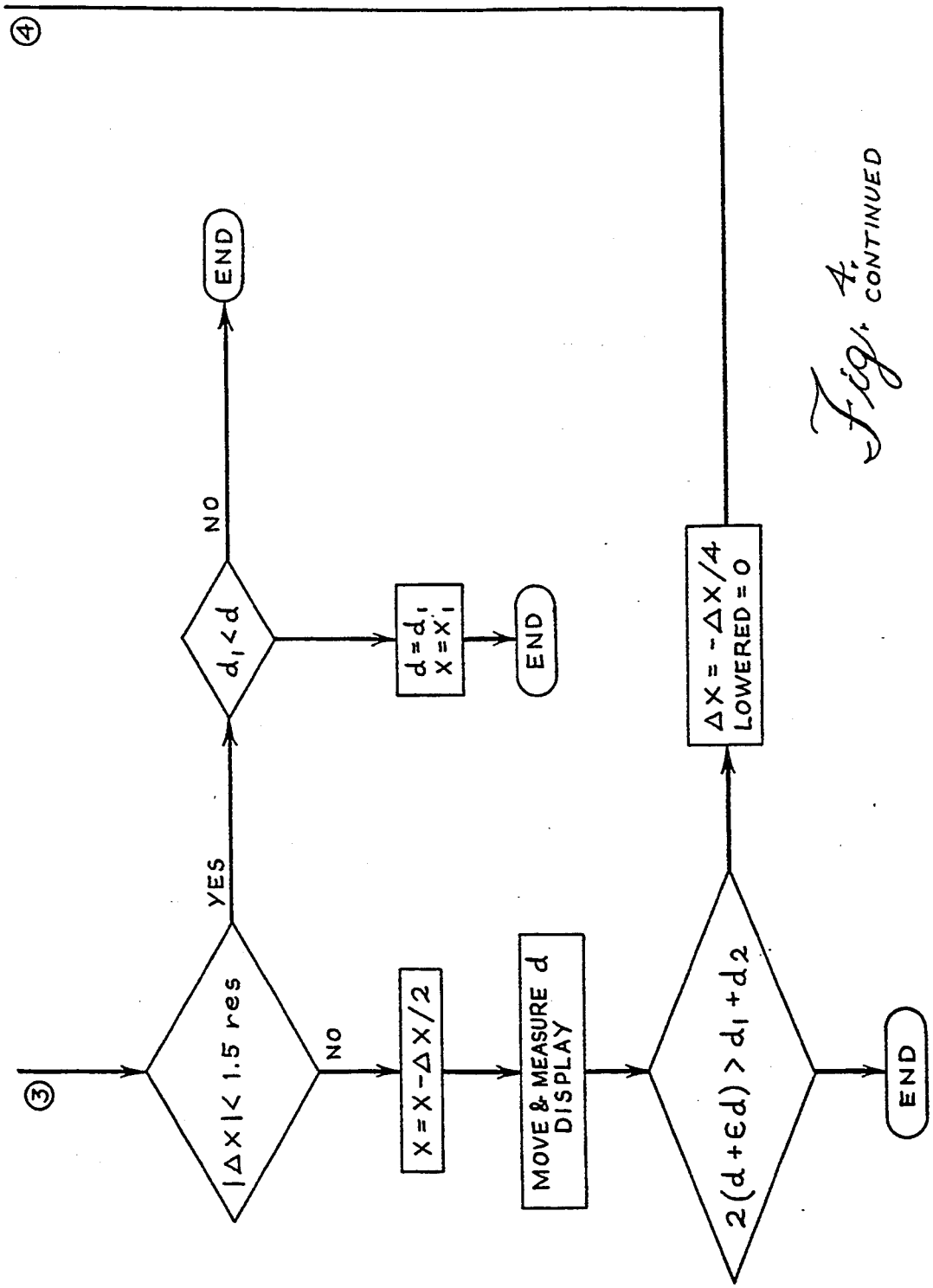

Generally speaking, in the present invention the rotating analyzer ellipsometer is employed as set forth in the flow charts of FIG. 3 and FIG. 4. Since the surface of wafer 10 and the overlying film 11 is generally planar a series of random points on the surface are selected and the thickness of the oxide film at these selected points measured using standard present day techniques. These measurements are reviewed and any excessively variant measurements discarded and the remainder averaged to establish a datum plane from which all further measurements are referred. If a computer is used to receive and calculate these measurements, the datum plane is established by repeating the loop designated in steps 30 through 34. Once the datum plane is established the system is set to recognize any departure from the datum plane, which exceeds a preset value, as a variation to be studied. As indicated above such variations can be protrusions extending above the surface or as depressions descending below the surface.

Once the datum plane and preset value have been established the surface 11 is scanned in a systematic manner by the ellipsometer and readings of the surface continuously taken and evaluated by the computer system (steps 32, 33 and feedback 34) until no variation in the reading is received which indicates that the surface 11 is uniform and without depression therein and the process is stopped step 35 or a reading is received that varies from the established datum plane by the selected preset amount. At this time further scanning of the surface is temporarily halted and the search mode step 36 is entered and measurement of the variation undertaken. For purposes of this generalized discussion only, it will be assumed that the variation is a depression.

The depth of the selected depression is established by searching for the maximum depth or lowest point of the depression using the sequence (step 37), generally shown in FIG. 4. FIG. 4 represents one computer program methodology in the form of a flow chart that can be used to carry out the sequence identified as step 37. A first depth measurement is taken somewhere within the depression. The coordinates of this location are recorded along with the measured depth at this location. Following the recording of this first depth and position the beam is moved slightly so that it remains within the depression but is located at a second position in the depression. The depth of this second position is also recorded along with its coordinates. Once two such depth measurements are made the difference therebetween is determined and the slope of the line between the recorded depths calculated, the slope of this line being indicative of the angle of the wall of the depression being studied. If the slope in the case of a depression is positive it indicates that the depth of the second measurement is not as great as the first. Then this establishes the position of the second measurement that is located higher on the wall and further away from the bottom of the depression than was the position of the first measurement.

Accordingly, the process is repeated, that is the beam is now moved to a third position away from the second position and on the other side of the first position from the second position. The depth at this third position is then measured and recorded along with the position coordinates. At this time the third measurement is compared to both the first and second recorded measurements. If the slope is negative with respect to both first and second measurements it means that the measurement position is now lower on the wall of the depression than either the first or second but that the bottom of the depression is still not reached. This search procedure is repeated through subsequent positions. The amount that the beam is moved in making these subsequent positions can be a fixed determined amount or can be variable depending upon desire of the operator. When the slope between any two sequential measurements goes to zero or goes positive it indicates that the bottom has either been reached or bypassed. At this time, a calculation, based on the obtained data from the last three measurements, can be made that will estimate where the lowest point in the depression will occur. In such a case the beam can be moved to the predicted location and the depth measured.

Alternately, the search sequence can be continued to find the lowest point. In such a case the incremental size of the movement can be reduced so the beam moves in smaller increments for higher accuracy.

A similar sequence is repeated (X5 thru X8). In either event one or more intermediate measurements is made between the positions. These intermediate measurements, if they continue to reflect a slope of zero indicates that a relatively flat bottom has been established and that the ultimate depth of the depression has been reached. If any of these intermediate measurements with respect to the two measurements whose slope is zero has a slope which is negative it indicates that the bottom is still not reached and still more intermediate measurements therebetween are required. Such intermediate measurements are taken until it is assured that the bottom of the depression has actually been reached. If desired the entire contour of the depression can be established by traversing and recordation of the remaining positions of the depression.

Once the bottom of the depression has been established the beam is either again placed in the scan mode and the surface again scanned until a new topographical feature is located and the above measurement sequence repeated. This scanning and measuring process is repeated across the entire surface area of the chip until all the topographical features of the surface have been measured.

Once the entire surface 11 has been scanned and all the topographical features recorded, a topographical map (step 40) of the display can be created and displayed from these recorded measurements. Once the display has been created the sequence for the wafer under study is ended (step 41).

Figure 5:
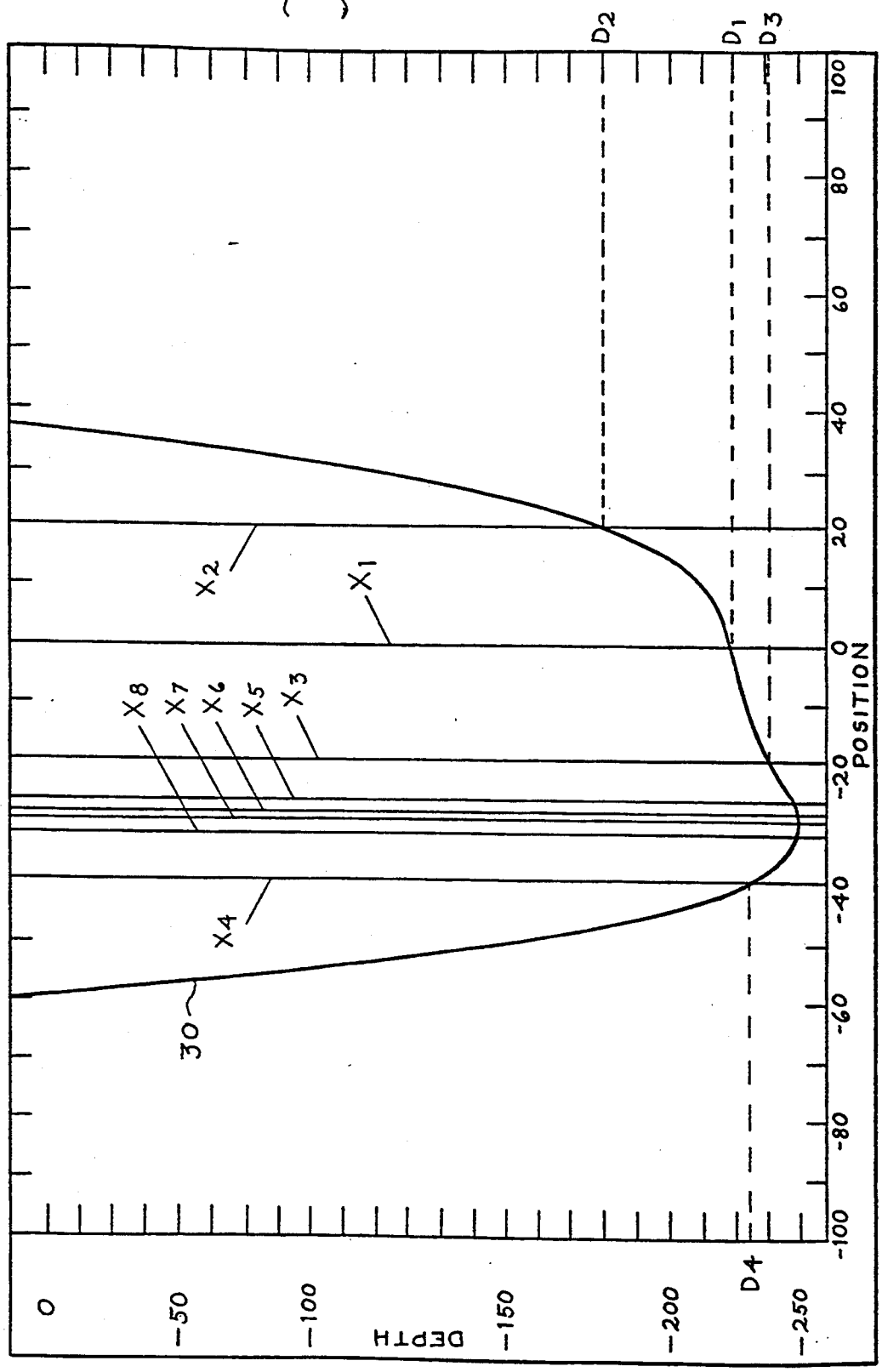
FIG. 5 is a plot of a typical cross section of a depression as measured by the present invention. Also, the film 11 can be comprised of layers of different materials as long as each is transparent or semi-transparent.

FIG. 5 shows the contour of an actual depression measured with the present invention. The present invention will be explained in greater detail in conjunction below using the steps set forth in flow chart form in FIGS. 3 and 4, and the actual depression contour shown in FIG. 5.

First, the surface 11 of the wafer to be studied is visually reviewed and a region which visually appears to have no significant topographical variation thereon is selected and a number of measurements are made in this selected region to establish a datum plane value. Such a featureless region can be deliberately designed on the surface of the wafer. Once a series of measurements is made and the base line established the beam is moved to an initial starting position for the scan to occur. The beam is then incrementally passed over the surface of the device in preselected steps. Alternately the beam may be deliberately directed to a selected position where a topographical feature exists.

As the surface 11 is scanned systematically by the ellipsometer, readings are continuously taken and evaluated by the computer system until a reading is received that varies from the established datum plane by the selected preset amount. At this time further scanning of the surface is halted and measurement of the variation undertaken. For purposes of discussion only, it will be assumed that the variation is one of the depressions 12 and its cross-section is as shown in FIG. 5.

A first depth measurement D1, is now taken at position X1 which may be anywhere within the depression. The coordinates of this position X, are recorded along with the measured depth D1. Following the recording of this first depth D1, and position X1 the beam is moved within the depression to a second position X2. The depth D2 at this second position X2 is also recorded along with its coordinates. Once two such depth measurements are made the difference therebetween is determined and the slope of this line between the recorded depths calculated. The slope of this line is indicative of the angle of the wall of the depression being studied. If the slope is positive it indicates that the position X2 of the second measurement is located higher on the wall of the depression and further away from the bottom of the depression than was the position of the first measurement.

Assuming such a positive slope is found the process is now repeated, such that the beam is moved to a third position X3 on the other side of the first position X1 from the second position X2. The depth D3 at this third position X3 is then measured and recorded along with the position coordinates. At this time the third measurement is compared to both the first and second recorded measurements. If the slope is negative with respect to both first and second measurement it means that the measurement position is now lower on the wall of the depression than either the first or second but does not indicate that the bottom of the depression has been reached. As indicated previously, a calculation can be made, at this time that will provide an estimate of the low point on the contour. In such a case the beam can be moved to that position and measurements made. Alternately, the search can be continued through a series of subsequent positions X4 to X8. The amount that the beam is moved in making these subsequent measurements can be a fixed, predetermined amount or can be variable depending upon desire of the operator. When the slope between any two of these subsequent sequential measurements goes position such as at position X4 or remains zero as though position X5 to X8 it indicates that the bottom has either been bypassed or reached. In either event a series of intermediate measurements is made between the positions exhibiting either the zero or positive slope measurement. These intermediate measurements, if they continue to reflect a slope of zero indicates that a relatively flat bottom has been found for the depression. If any of these intermediate measurements with respect to the two measurements whose slope is zero has a slope which is negative it indicates that the bottom is still not reached and still more measurements therebetween are required. Such intermediate measurements are taken until it is assured that the bottom of the depression has actually been reached. If desired the entire contour of the depression can be established by traversing and recording of the remaining portions of the depression.

Once the desired result is achieved, i.e. the bottom or contour of the depression has been established, the beam is again placed in the scan mode and the surface again scanned until a new topographical feature is located and the above sequence repeated. This scanning and measuring process is repeated across the entire surface area 11 of the chip 10 until all the topographical features of the surface have been measured.

Once the entire surface has been scanned and all the topographical features recorded a topographical map of the display can be created and displayed from these recorded measurements.

Table I set forth below shows the program used to implement the method of the present invention, in accordance with the flow chart of FIG. 4.

This program is written in the IBM C/2 language and is compatible with most C language supports.

TABLE I
DETERMINATION OF FUNTIONS AND VARIABLES

```
/* global variables*/
struct result2 {                    /* structure for reading
                                       variables */
    float p[2];                     /* two variables of a reading
                                       */
    char status[32];                /* status of a reading */
};
int abort_flag=0,                   /* operator to abort running
                                       software when -1 */
    err_flag=0,                     /* unexpected error occures
                                       when -1 */
    iow=0,                          /* index of wafers being
                                       measured */
    ios=0;                          /* index of current sites */
double x=0.0,                       /* absolute position to move
                                       stage & currently from
                                       encoder */
       res_x=0.01,                  /* smallest increment to move
                                       stage */
       res_d=0.5,                   /* thickness repeatability for
                                       search_d */
       dxinit=0.06;                 /* initial increment of moving
                                       stage for search_d */
struct result2 data[16] [100];
                                    /* global reading data */
                                    /* 16 wafers max, 100 sites
                                       max */
/* global functions */              /* partially fictitious
                                       functions */
int move_stage ();                  /* to move stage with absolute
                                       x and y */
int measure_site();                 /* to measure PSI & DELTA
                                       and compute variable(s) */
int interface();                    /* to display data and read
                                       inputs from keyboard */
void error_msg(char *);             /* to display and to record a
                                       string */
void instr_msg(char *);             /* to display instructional
                                       string */
int move_stage () {                 /* returns 0 when successed,
                                       -1 when failed */
    return(0);
}
int measure_site() {                /* returns 0 when successed,
                                       -1 when failed */
    return(0);
}
int interface() {                   /* returns 0 when abort key is
                                       pressed */
    return(1);
}
double get_d() {
    if (move_stage()) return (-1);
    if (measure_site()) return (-1);
    if (!interface()) {
        abort_flag=1;
        instr·msg("being aborted ... ");
        return(-1);
    }
    return(data[iow] [ios].p[0]);   /* thickness */
                STEP 37
double search_d() {                 /* returns thickness or -1 as
                                       failure */
    register j=0;                   /* loop counter */
    int max=10,                     /* maximum loops allowed */
    lowered=0;                      /* trend flag -1 means 2nd
                                       thickness on the downward
```

TABLE I-continued
DETERMINATION OF FUNTIONS AND VARIABLES

```
                                       trend */
    double d,                       /* current thickness */
           d1, d2                   /* older thicknesses */
           x1,                      /* older position of stage
                                       than x */
           dx;                      /* dynamical increment of
                                       x */
    d=data[iow] [ios].p[0];         /* assigns the global variable
                                       to tempory d */
    dx=dxinit;
    while(j++<max) {
        d1=d;
        x1=x;
        x=x+dx;
        if ((d=get_d())<0) return (-1);
        if (d<d1-res_d) {           /* on the right direction of
                                       stage movement */
            d2=d1;
            lowered=-1;             /* sets flag that it continues
                                       on the same trend */
            continue;
        }
        if (d>d1+res_d) {           /* on the wrong direction */
            if (lowered) {          /* the minimum found */
                x=x1+(d2-d)/(d-2*d1+d2)*dx/2.0;
                if ((d=get_d())<0) return(-1);
                if ((d+res_d)<d1 && fabs(dx)<dxinit) return (d);
                if (fabs(dx)<=4*res_x) return(d);
                dx-dx/4.0;
                lowered=0;
                continue;
            } else {                /* switches the direction */
                dx=-dx;
                d2=d;               /* switches all values and
                                       sets same trend flag */
                d=d1;
                x=x1;
                lowered==1;
                continue;
            }
        }
        if                          /* to check
        (fabs(dx)<=1.5-
        *res_x) {                   increment compared
                                       with resolution */
            if (d1<d) {
                d=d1;
                x=x1;
            }
            return(d);              /* no need to find minimum
                                       thickness further */
        }
        d2=d;                       /* to measure thickness
                                       between two points */
        x=x-dx/2.0;
        if ((d=get_())<0)
        return(-1);
        if (2*(d+res_d)>d1+d2 && 2*(d-res_d)<d1+d2)
            return(d);              /* all readings are
                                       essentially same */
        if (d>d2) {                 /* to select minimum
                                       thickness */
            if (d1>d2) {
                d=d2;
                x=x+dx/2.0;
            } else {
                d=d1;
                x=x-dx/2.0;
            } /* endif */
        }
        dx=dx/4.0;                  /* refresh search with
                                       smaller increments */
        lowered=0;
    }
    err_flag=-1;
    error_msg("exceeded maximum iteration during search
    minimum thickness");
    return(-1);
```

TABLE I-continued

DETERMINATION OF FUNTIONS AND VARIABLES

}

While the present invention has been particularly shown and described with reference to preferred embodiments thereof, it will be understood by those skilled in the art that various changes in form and detail may be made therein without departing from the spirit and scope of the invention.

What is claimed is:

1. A method of locating a predetermined variation in the surface of a film such as selected depression or elevation on a film deposited on a surface and for measuring the depth of the depression or height of the elevation comprising the steps of:

scanning a light beam, from an ellipsometer having a rotating analyzer and a dual output optical annular encoder mounted on the same shaft as said rotating analyzer, across the surface of a film to be scanned, establishing a datum plane based on the average level of the surface of the film, systematically scanning the surface of the film with the beam until a predetermined variation from said datum plane is located, on the surface of the film, incrementally stepping the beam around and across the located variation, measuring the beam reflected at various points along the variation to determine the contour of the variation by establishing the slope of the variation between various measurements, establishing the point of greatest extent of the variation by determining when the measured slope passes through to zero, and measuring the distance of the established point of greatest extent of the variation with respect to the established datum plane of the film.

2. The method of claim 1 wherein there is further provided the step of locating a particular variation on a surface by comparing the measured value of the established point of greatest extent of the variation with a preselected value.

3. The method of claim 1 wherein there is further provided the step of recording and displaying the extent of each recorded variation and its location to provide a map of the topology of the film.

4. The method of claim 1 wherein said establishing step consists of estimating the point of greatest variation from received data and directing the beam to said estimated point for further measurements.

* * * * *